United States Patent [19]
Pfleiderer et al.

[11] Patent Number: 5,945,524
[45] Date of Patent: Aug. 31, 1999

[54] PROCESS FOR THE CHEMICAL SYNTHESIS OF OLIGONUCLEOTIDES

[75] Inventors: Wolfgang Pfleiderer, Constance; Frank Bergmann, Weissenberg, both of Germany

[73] Assignee: Hoechst Aktiengesellschaft, Frankfurt am Main, Germany

[21] Appl. No.: 08/487,229

[22] Filed: Jun. 7, 1995

Related U.S. Application Data

[62] Division of application No. 08/437,566, May 9, 1995, Pat. No. 5,631,362, which is a continuation of application No. 08/219,239, Mar. 28, 1994, abandoned, which is a continuation of application No. 07/757,924, Sep. 12, 1991, abandoned.

[30] Foreign Application Priority Data

Sep. 14, 1990 [DE] Germany .............................. 40 29 244
Apr. 9, 1991 [DE] Germany .............................. 41 11 363

[51] Int. Cl.$^6$ .............................. C07H 1/00; C07H 31/70
[52] U.S. Cl. .................. 536/25.3; 536/25.31; 536/25.34; 536/27.1; 536/27.21; 536/27.61; 536/27.62; 536/27.63; 536/27.8; 536/28.54
[58] Field of Search ................................ 536/25.3, 25.31, 536/25.34, 27.1, 27.21, 27.61, 27.62, 27.63, 27.8, 28.54

[56] References Cited

U.S. PATENT DOCUMENTS 3,781,310 12/1973 Meininger et al. .

FOREIGN PATENT DOCUMENTS

A-0267996 5/1988 European Pat. Off. .
A-0272928 5/1988 European Pat. Off. .
A-1953600 5/1971 Germany .

OTHER PUBLICATIONS

E. Winnacker, "From Genes to Clones," 1987, Chaoter 2.3.
C. Lehmann et al., "Solid–phase synthesis of oligoribonucleotides using 9–fluorenylmethoxycarbonyl (Fmoc) for 5'–hydroxyl protection," Nucleic Acid Research, vol. 17, No. 7, 2379–2390, Apr. 1989.

*Primary Examiner*—James O. Wilson
*Attorney, Agent, or Firm*—Finnegan, Henderson, Farabow, Garrett & Dunner, L.L.P.

[57] ABSTRACT

Use of a dansylethoxycarbonyl group as base-labile 5'-hydroxyl protective group in the chemical synthesis of DNA and RNA and suitable synthetic processes.

The ease of detection of the dansyl protective group and the ease of elimination from the sugar residue of the nucleotide without side reactions make oligonucleotide synthesis possible with high yields in very small quantities.

42 Claims, No Drawings

PROCESS FOR THE CHEMICAL SYNTHESIS OF OLIGONUCLEOTIDES

This is a division of application Ser. No. 08/437,566, filed May 9, 1995, now U.S. Pat. No. 5,631,362, which is a continuation of Ser. No. 08/219,239 filed Mar. 28, 1994, now abandoned, which is a continuation of Ser. No. 07/757,924 filed Sep. 12, 1991, abandoned.

The chemical polycondensation of mononucleotides is an important method for the preparation of deoxyribonucleic acid (DNA) or ribonucleic acid (RNA).

A fundamental problem in the chemical synthesis of DNA or RNA is to find suitable protective groups for the amino and hydroxyl groups on the nucleoside bases and the sugar residues. These protective groups must, on the one hand, be stable under the conditions of the polycondensation reaction, i.e. during the formation of the phosphodiester linkage, and must, on the other hand, be sufficiently labile for it to be possible to remove them again at the end of the reaction without cleaving the phosphodiester linkage (H. G. Khorana; Pure Appl. Chem. 17 (1968) 349).

The chemical synthesis of RNA is particularly difficult because the ribose sugar residue carries two hydroxyl groups, both of which must be protected. Moreover, before each polycondensation step, the protective group on the 5'-hydroxyl group must be eliminated again selectively, i.e. without eliminating the 2'-hydroxyl protective group. On the other hand, the protective group on the 2'-hydroxyl group must be eliminated only at the end of the RNA synthesis, specifically under conditions which do not lead to any cleavage or isomerization of the phosphodiester linkages (C. B. Reese, Nucleic Acids and Molecular Biology, Vol 3 (F. Eckstein & D. M. J. Lilley eds.) Springer-Verlag, Weinheim).

One possibility for the selective elimination of the 5'-hydroxyl protective group without eliminating the 2'-hydroxyl protective group is achievable by combining a base-labile 5'-hydroxyl protective group with an acid-labile 2'-hydroxyl protective group (Chr. Lehmann et al. (1989) Nucleic Acids Res. 17, 2379–2390, No. 7). The use of a base-labile 5'-hydroxyl protective group is also advantageous in the synthesis of DNA because there is generally no cleavage under the mild non-acid hydrolysis conditions of the phosphodi- and -triester linkages already formed in the synthesis. In addition, depurination of the nucleotides as described by E. Sonveaux (E. Sonveaux (1986), Bioorganic Chemistry 14, 286) is avoided under the mild non-acid hydrolysis conditions. Another requirement to be met by the 5'-hydroxyl protective group in DNA as well as in RNA synthesis is that the protective group be detectable easily and highly sensitively. It is possible in this way to follow especially well the degree of conversion in the individual reaction steps and to achieve conversion which is as complete as possible. This makes it possible to prepare especially long oligonucleotides in high yield. This also permits small synthesis mixtures in the nanomolar to picomolar range to be carried out.

It has now been found, surprisingly, that the dansylethoxycarbonyl group (Dans-EOC) can be employed as base-labile 5'-hydroxyl protective group in chemical oligonucleotide synthesis.

The invention therefore relates to 1. a process for the preparation of the compound of the formula (I)

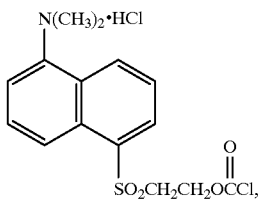

which comprises reacting the compound of the formula (II)

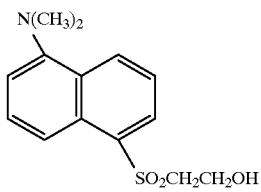

with a chlorocarbonyl donor.

2. A compound of the formula (IIIa) or (IIIb)

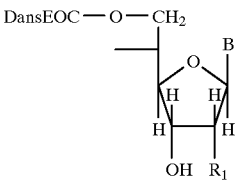

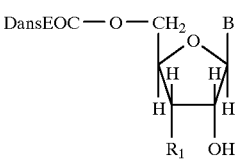

in which $R_1$ is hydrogen or, independently of one another, a group of the formula

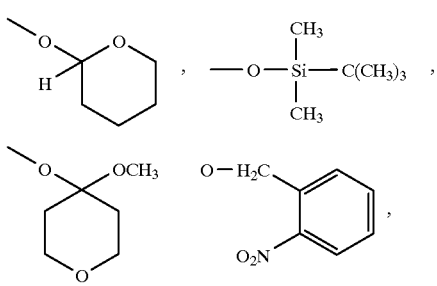

-continued

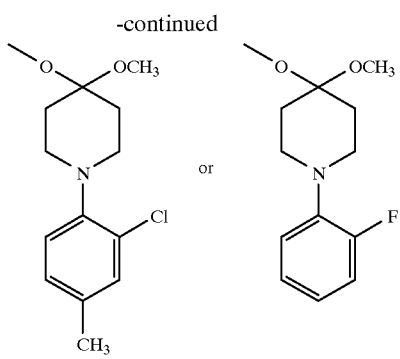

or and
B is

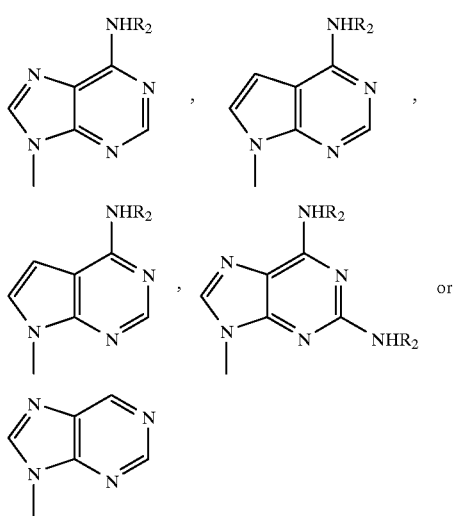

or with R₂ being, in each case independently of one another, a group of the formula

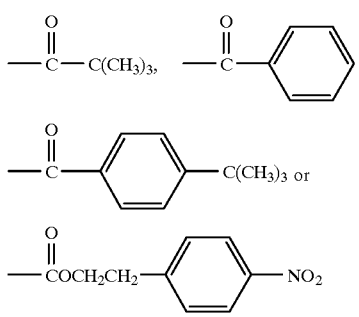

or
B is

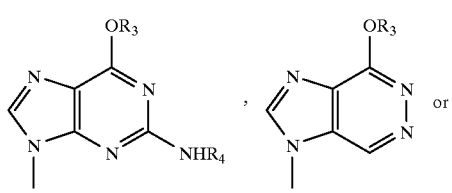

or

-continued

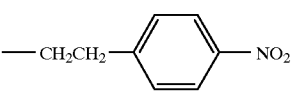

with R₃ being hydrogen or

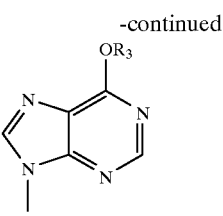

and
R₄ being

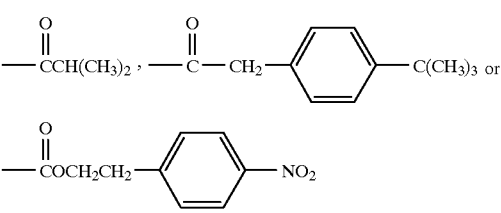

or
B is

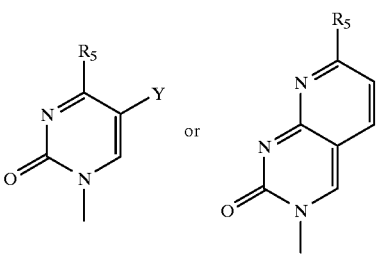

with R₅ being —OH,

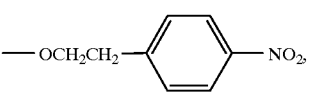

Y=H, alkyl ($C_1$–$C_4$), especially $CH_3$,

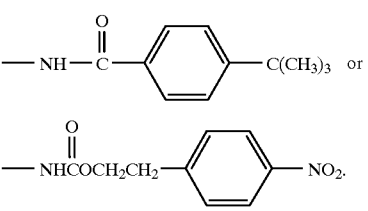

3. A process for the preparation of a compound of the formula (IIIa) or (IIIb) by reacting the compound of the formula (I) with an appropriate compound of the formula (IVa) or (IVb)

(IVa)

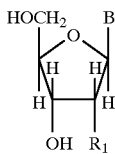

(IVb)

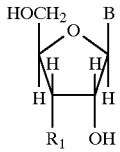

in which $R_1$ and B have the above meaning, in the presence of a base, preferably pyridine or a mixture composed of tetrahydrofuran, dioxane, methylene chloride, chloroform and/or acetonitrile and of a compound of the formula $NR_{20}R_{21}R_{22}$ in which $R_{20}$, $R_{21}$ and $R_{22}$ are, identically or independently differently, hydrogen or the $C_1$–$C_4$-alkyl group, preferably a trimethyl, triethyl or diisopropyl group.

4. A compound of the formula (Va) or (Vb)

(Va)

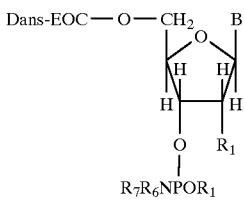

(Vb)

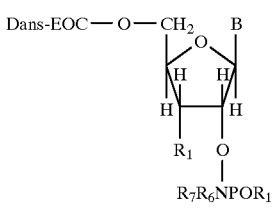

in which

DansEOC, $R_1$ and B have the abovementioned meaning, and $R_6$ and $R_7$ are, identically or independently differently, a $C_1$–$C_8$-alkyl, preferably an isopropyl or $C_5$–$C_{12}$-cycloalkyl group, preferably up to $C_8$, benzyl or phenyl or, together with the nitrogen atom to which they are bonded, a saturated or unsaturated heterocyclic ring which can optionally contain further hetero atoms and substituents and $R_8$ is group of the formula

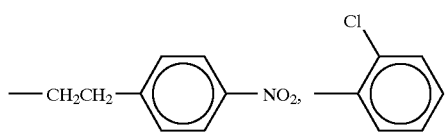

-continued

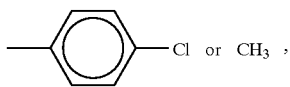

or a benzyl group which is unsubstituted or ring-substituted one or more times, preferably unsubstituted, where the substituent(s) is, independently of one another, a halogen, a $C_1$–$C_4$-alkyl, nitro, methoxy or carboxyl group.

5. A process for the preparation of a compound of the formula (Va) or (Vb) by reacting the compound of the formula (IIIa) or (IIIb) with a compound of the formula (VI)

(VI)

in which $R_6$, $R_7$ and $R_8$ have the above meaning, and Z is chlorine or bromine or a radical of the formula —$NR_9R_{10}$ where the same radicals as for $R_6$ are suitable for $R_9$ and $R_{10}$, independently of one another, when Z equals chlorine, in the presence of a base, preferably pyridine or a mixture of tetrahydrofuran, dioxane, methylene chloride, chloroform and/or acetonitrile with a $C_1$–$C_4$-trialkylamine, preferably a trimethyl-, triethyl- or diisopropylethyl amine, or when Z is a radical of the formula —$NR_9R_{10}$, then in the presence of a compound of the formula $[HNR_{11}R_{12}R_{13}]^{(+)}X^{(-)}$ where $R_{11}$, $R_{12}$ and $R_{13}$ are, identically or independently differently, a $C_1$–$C_4$-alkyl group and X is halogen, especially chlorine, or tetrazole, preferably in the presence of tetrazole.

6. A process for the preparation of oligonucleotides from compounds of the formula (Va) and/or (Vb), which comprises a compound of the formula (Va) or (Vb)
 1. being reacted with a compound of the formula (VIIa) or (VIIb)

(VIIa)

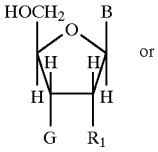

(VIIb)

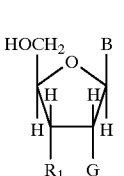

in which B and $R_1$ have the abovementioned meaning, and G has the same meaning as $R_1$ or is a polymeric support which is bonded via the 2'-hydroxyl or 3'-hydroxyl group of the compound of the formula (VIIa) or (VIIb),
 2. the resulting compounds being oxidized
 3. the dansylethoxycarbonyl group being eliminated,
 4. the resulting compound being reacted with a compound of the formula (Va) or (Vb) and
 5. reaction steps 2–4 being repeated up to the required chain length.

7. A compound of the formula (VIIIa) or (VIIIb)

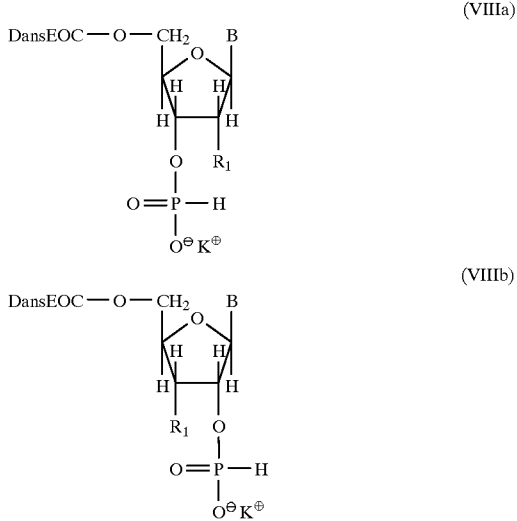

(VIIIa)

(VIIIb)

in which DansEOC, $R_1$ and B have the abovementioned meaning, and $K^{(+)}$ is a cation, especially $[HN(C_2H_5)_3]^{(+)}$.

8. A process for the preparation of a compound of the formula (VIIIa) or (VIIIb) by reacting a compound of the formula (IIIa) or (IIIb) with a compound of the formula (IX)

$$PR_{14}R_{15}R_{16} \qquad (IX)$$

in which $R_{14}$, $R_{15}$ and $R_{16}$ are, identically or independently differently, hydrogen or a $C_1$–$C_8$-alkyl, $C_1$–$C_8$-fluoroalkyl or aryl group, preferably a 2,2,2-trifluoroethyl, 1,1,1,3,3,3,-hexafluoro-2-propyl, ethyl or phenyl group in the presence of a base.

9. A process for the preparation of a compound of the formula (VIIIa) or (VIIIb) by reacting a compound of the formula (IIIa) or (IIIb) with a compound of the formula (X)

$$PR_{17}R_{18}R_{19} \qquad (X)$$

in which $R_{17}$, $R_{18}$, and $R_{19}$ are, identically or independently differently, chlorine, bromine or a $C_1$–$C_8$-alkylamino or 1,2,4-triazolyl group, preferably a 1,2,4-triazolyl group, in the presence of a base with subsequent hydrolysis.

10. A process for the preparation of oligonucleotides from compounds of the formula (VIIIa) and/or (VIIIb), which comprises a compound of the formula (VIIIa) or (VIIIb)
  1. being reacted with a compound of the formula (VIIa) or (VIIb),
  2. the dansylethoxycarbonyl group being eliminated,
  3. the resulting compound being reacted with a compound of the formula (VIIIa) or (VIIIb),
  4. reaction steps 2 and 3 being repeated up to the required chain length and
  5. the resulting oligonucleotide being oxidized.

To introduce the dansylethoxycarbonyl group into the nucleoside, 2-dansylethyl chloroformate hydrochlorid was reacted with a nucleoside in which, depending on the nucleoside, the amino and hydroxyl groups in the nucleoside base are protected by suitable groups. Examples of suitable protective groups for the 6-amino group of adenine are the t-butyloxycarbonyl, benzoyl, 4-(t-butyl)benzoyl or para-nitrophenylethyloxycarbonyl group, especially the benzoyl or the para-nitrophenylethyloxycarbonyl group.

Examples suitable for the 2-amino group of guanine are the isobutyryl, 4-(t-butyl)phenylacetyl or para-nitrophenylethyloxycarbonyl group, especially the isobutyryl or the para-nitrophenylethyloxycarbonyl group. The 6-hydroxyl group of guanine and the 4-hydroxyl group of uracil either generally remain unprotected or are protected by a para-nitrophenylethyl group. In the case of cytosine, the 4-amino group is protected, for example, by a benzoyl, 4-(t-butyl)benzoyl or para-nitrophenylethyloxycarbonyl group, especially the benzoyl or the para-nitrophenylethyloxycarbonyl group. Thymidine generally remains unprotected. The 3-N group in uridine is protedted, for example, by a Boc or an amisoyl group.

It is also possible in place of the natural nucleoside bases to use modified nucleoside bases whose amino or hydroxyl groups can be protected in an analogous manner by the abovementioned protective groups. Examples of nucleosides with modified bases are inosine, 8-aza-7-deazaadenosine, tubercidin, nebularine, xanthosine, 2-aminoadenosine or pyridopyrimidine nucleosides. The nucleosides can be bought, and the introduction of the individual protective groups can be carried out, for example, by the method C. Lehmann et al. (1989), C. B. Reese (1989) ["The Chemical Synthesis of Oligo and Polyribonucleotides" in Nucleic Acids and Molecular Biology 3, F. Eckstein & D. M. J. Lilley (eds.), Springer Verlag Berlin, Heidelberg], E. Sonveaux (1986), Bioorganic Chemistry 14, 274–325 or E. Uhlmann and A. Peyman (1990), Chemical Reviews 90, 543–584, No. 4.

When ribonucleotides are used it is necessary also to protect the 2'-hydroxyl group of the ribose residue, in addition to the hydroxyl and amino group of the nucleotide bases. As already mentioned, it is important for RNA synthesis to be able, by the choice of a suitable combination of 5'-hydroxyl and 2'-hydroxyl protective group, to remove the 5'-hydroxyl protective group selectively, i.e. without elimination of the 2'-hydroxyl protective group.

It is now possible to eliminate selectively the dansylethoxycarbonyl group as 5'-hydroxyl protective group under non-acid conditions in the presence of acid-labile 2'-hydroxyl protective groups. Examples of acid-labile 2'-hydroxyl protective groups which can be used are the 4-methoxy-4-tetrahydropyranyl, tetrahydropyranyl, t-butyldimethylsilyl, 2-nitrobenzyl, 1-(2-chloro-4-methylphenyl)-4-methoxy-4-piperidinyl, or the 1-(2-fluorophenyl)-4-methoxy-4-piperidinyl group. The dansylethoxycarbonyl group is preferably eliminated in an aprotic polar solvent, especially acetonitrile or pyridine having 1 to 3, preferably 1.5 to 2.5 mole equivalents of DBU (=1,5-diazabicyclo[5.4.0]undec-5-ene). It is possible as an alternative to employ bases such as TMG ($=N^1,N^1,N^2$, $N^2$tetramethylguanidine) or $C_1$–$C_4$-trialkylamines such as, triethylamine for the elimination.

2-Dansylethyl chloroformate hyrochloride was prepared as starting compound for the 5'-hydroxyl protective group of the ribose or deoxyribose residue by reacting 2-dansylethanol with a chlorocarbonyl donor such as, for example, trichloromethyl chloroformate, (diphosgene) and/or phosgene, preferably trichloromethyl chloroformate in the presence of a polar, aprotic solvent. In a preferred embodiment, the reaction was carried out in the presence of a single polar, aprotic solvent, especially in the presence of acetonitrile. The molar ratio of 2-dansylethanol to the chlorocarbonyl donor was 0.5–1 to 1–2, preferably 1 to 1–2, in particular 1 to 1.5–2. The reaction temperature was in a range from −20° C. to the boiling point of the reaction mixture, preferably from −5° C. to +20° C., in particular from 0° C. to 5° C.

The process according to the invention results in 2-dansylethyl chloroformate hydrochloride as a pure product whose composition was confirmed by elemental analysis. This is so surprising because A. Takadate et al. (A. Takadate et al. (1983) Yakugaku Zasshi 103, 982–966) reacted 2-dansylethanol with trichloromethyl chloroformate to give a product whose melting point is about 20° C. lower than the product synthesized in the said process. 2-Dansylethanol can be prepared, for example, by the method of S. Goya et al. (S. Goya et al (1981) Yakugaku Zasshi 101, 1164).

The reaction of 2-dansylethyl chloroformate hydrochloride with the protected nucleoside can be carried out, for example, in analogy to the reaction with 9-fluorenylmethoxycarbonyl chloride by the method of C. Lehmann et al. (1989) in the presence of a base. Suitable as base are organic bases, especially pyridine or a mixture composed of tetrahydrofuran, dioxane, methylene chloride, chloroform and/or acetonitrile and of a compound of the formula

$NR_{20}R_{21}R_{22}$ in which $R_{20}$, $R_{21}$ and $R_{22}$ are, identically or independently differently, hydrogen or a $C_1$–$C_4$-alkyl, preferably a trimethyl, triethyl or diisopropyl group. If the substrate used therefore is a 2'-protected ribonucleoside, the result is a mixture of products composed of the dansylethyloxycarbonyl-ribonucleoside and the bis-dansylethyloxycarbonyl-ribonucleoside as by-product. This mixture of products can be employed directly in the subsequent phosphorylation reaction. It is also possible, and preferable, for the mixture to be purified by, for example, flash chromatography. The bis-dansylethyloxycarbonyl-ribonucleoside which has been removed can then subsequently be cleaved, for example with DBU, into the dansyl-free ribonucleoside which in turn can be used as starting compound for the dansylation reaction.

To synthesize 2',5'-linked oligoribonucleotides which, for example, as tri- or tetraadenylate inhibit protein biosynthesis (Kerr, I. M. & Brown, R. E. (1978) Proc. Natl. Acad. Sci. USA. 75, 256–260), it is possible to react a nucleoside which is protected in accordance with the above description and has a free 2'-hydroxyl group with 2-dansylethyl chloroformate hydrochloride in an analogous manner.

The dansylated nucleoside with the 2'- or 3'-hydroxyl group still free on the sugar residue is generally phosphitylated. It is possible to use as phosphitylation reagent, for example, a compound of the formula (VI)

$$\underset{\underset{R_7R_6NPOR_8,}{|}}{Z} \qquad (VI)$$

in which $R_6$ and $R_7$ are, identically or independently differently, $C_1$–$C_8$-alkyl, preferably an isopropyl or $C_5$–$C_{12}$-cycloalkyl group, preferably up to $C_8$, a benzyl or a phenyl group, or, together with the nitrogen atom to which they are bonded, a saturated or unsaturated heterocyclic ring which can optionally contain further hetero atoms and substituents $R_8$ is a group of the formula

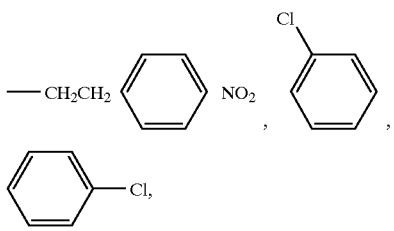

or $CH_3$,
or a benzyl group which is unsubstituted or ring-substituted one or more times, preferably unsubstituted, where the substituent(s) is, independently of one another, for example a halogen, a $C_1$–$C_4$-alkyl, nitro, methoxy or carboxyl group,
z is chlorine, bromine or a radical of the formula —$NR_9R_{10}$ where $R_9$ and $R_{10}$ are, identically or independently differently, a $C_1$–$C_8$-alkyl, preferably an isopropyl or $C_5$–$C_{12}$-cycloalkyl group, preferably up to $C_8$, a benzyl or a phenyl group.

Preferably used as phosphitylation reagent was a compound of the formula (VII) with Z=chlorine, $R_6$ and $R_7$ each an isopropyl radical and $R_8$ equals a group of the formula

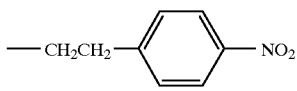

The reaction was generally carried out in an organic solvent such as tetrahydrofuran or methylene chloride, preferably methylene chloride, in the presence of 1 to 8, preferably 1 to 6, in particular 1 to 4, mole equivalents of an organic base such as pyridine or a mixture of tetrahydrofuran (THF), dioxane, methylene chloride, chloroform and/or acetonitrile and of a $C_1$–$C_4$-trialkylamine, preferably a trimethyl-, triethyl- or diisopropylethyl-amine, especially diisopropylethyl-amine. If Z is a radical of the formula —$NR_9R_{10}$, the reaction was preferably carried out in the presence of a compound of the formula $(HNR_{11}R_{12}R_{13})^{(+)}$ $X^{(-)}$ where $R_{11}$, $R_{12}$ and $R_{13}$ are, identically or independently differently, a $C_1$–$C_4$-alkyl group and $X^{(-)}$=halide, especially a chloride, or a tetrazolide, or a tetrazole, preferably in the presence of tetrazole. The molar ratio of dansylated nucleoside to phosphitylation reagent was 1 to 1–4, preferably 1 to 2–4, in particular 1 to 2.5–3.5.

The compounds of the formula (Va) or (Vb) obtained in this way can subsequently be employed for oligonucleotide synthesis. In this, the sugar residues of the nucleotides are deoxyribose for DNA synthesis and ribose for RNA synthesis, but mixtures of deoxyribose and ribose for the synthesis of an oligonucleotide composed of regularly or irregularly arranged deoxyribose and ribose sugar residues are also possible. Furthermore, the oligonucleotide can have a regular or irregular structure composed of mononucleotides of the formula (Va) and (Vb). The oligo- and polynucleotide synthesis can be carried out in a manner analogous to the phosphoramidite method as described, for example, by Chr. Lehmann et al. (1989).

There are in principle two possibilities for the synthesis of oligonucleotides. On the one hand, the synthesis can take place in solution, for example by the method described by C. B. Reese (C. B. Reese (1989) "The Chemical Synthesis of Oligo- and Poly-ribonucleotides" in Nucleic Acids and Molecular Biology (F. Eckstein & D. M. J. Lilley, eds.) 3, 164–181).

On the other hand, the oligonucleotide synthesis can take place on the solid phase, for example on nucleoside-functionalized glass, (K. P. Stengele & W. Pfleiderer (1989) Nucleic Acids Res. Symp. Ser. 21, 101, K. P. Stengele & W. Pfleiderer (1990) Tetrahedron Lett. 31, 2549 or Chr. Lehmann et al. (1989) Nucleic Acids Res. 17, 2379–2390, No. 7). In general, the solid-phase synthesis is the preferred method.

For this, the following reaction sequence was preferably chosen:

1. Reaction of a compound of the formula (Va) or (Vb) with the nucleoside of the formula (VIIa) or (VIIb)

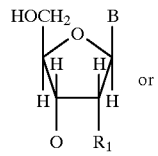

(VIIa)

or

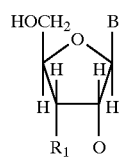

(VIIb)

in which B and $R_1$ have the abovementioned meaning, and G has the same meaning as $R_1$ or is a polymeric support which is bonded via the 2'-hydroxyl or 3'-hydroxyl group of the compound of the formula (VIIa) or (VIIb), in the presence of a weak acid, for example tetrazole or p-nitrophenyltetrazole.

2. Trapping of unreacted compounds of the formula (VIIa) or (VIIb), for example with acetic anhydride.
3. Oxidation to phosphate, phosphoramidate or to the thiophosphate, for example with iodine, sulfur or iodine/amine.
4. Elimination of the dansylethoxycarbonyl group, for example with DBU in acetonitrile.
5. Reaction of the resulting support-linked compound with a compound of the formula (Va) or (Vb).
6. Repetition of reaction steps 2 to 6 to give the required chain length of the oligonucleotide.

The compounds of the formula (Va) or (Vb) and (VIIa) or (VIIb) were preferably reacted at −20 to +100° C., in particular at room temperature in the presence of, for example, tetrazole or para-nitrophenyltetrazole as weak acids. The oxidation was carried out at a temperature of −80 to 100° C., preferably at −20 to +60° C., in the presence of iodine, sulfur or iodine in the presence of an amine (A. Jäger et al. Biochemistry 27, 7237 (1988)). When a mixture of iodine, water and an organic base such as lutidine or pyridine was used, the oxidation was preferably carried out at room temperature. On the other hand, when a mixture of elemental sulfur, toluene and an organic base was used, the oxidation was preferably carried out at 60° C.

The synthesized oligonucleotides were generally composed of 2 to about 200, preferably 2 to 100, in particular 2 to 20 mononucleotides.

As an alternative to the phosphitylation, the dansylated nucleoside with the 2'- or 3'-hydroxyl group still free on the sugar residue can also be converted into the H-phosphonate of the formula (VIIIa) or (VIIIb).

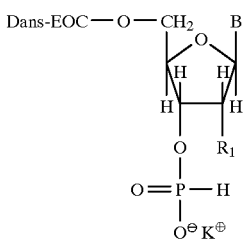

(VIIIa)

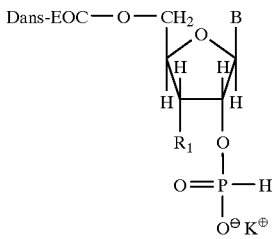

(VIIIb)

in which DansEOC, $R_1$ and B have the abovementioned meaning, and $K^{(+)}$ is a cation, especially $[NH(C_2H_5)_3]^{(+)}$ (R. Strömberg, Chem. Commun. 1987, 1; B. C. Froehler, P. G. Ng, M. D. Matteucci, Nucleic Acids Res. 14 (1986) 5399; M. Tahalu et al., Chem. Lett. 1988, 1675).

This generally entails a compound of the formula (IIIa) or (IIIb) being reacted with a compound of the formula (IX) or (X)

$$PR_{14}R_{15}R_{16} \qquad (IX)$$

$$PR_{17}R_{18}R_{19} \qquad (X)$$

in which $R_{14}$, $R_{15}$ and $R_{16}$ are, identically or independently differently, hydrogen or a $C_1$–$C_8$-alkyl, $C_1$–$C_8$-fluoroalkyl or aryl group and $R_{17}$, $R_{18}$ and $R_{19}$ are, identically or independently differently, chlorine, bromine or a $C_1$–$C_8$-alkylamino or a 1,2,4-triazolyl group.

The dansylated nucleoside was preferably reacted with bis(2,2,2-trifluoroethyl) H-phosphonate, bis(1,1,1,3,3,3-hexafluoro-2-propyl) H-phosphonate, triethyl phosphite, triphenyl phosphite or with $PCl_3$, tri(dialkylamino) phosphines or tris(1,2,4-triazolyl) phosphite, preferably tris (1,2,4-triazolyl) phosphite, particularly preferably with $PCl_3$ after activation with imidazole/triethylamine with subsequent hydrolysis to the H-phosphonate.

The reaction was carried out in an organic solvent such as tetrahydrofuran or methylene chloride, preferably methylene chloride, in the presence of 1–50 mole equivalents, preferably 10–50, in particular 30–50 mole equivalents of an organic base such as $C_1$–$C_4$-trialkylamine or N-$C_1$–$C_4$-alkylmorpholine, preferably N-methylmorpholine. The molar ratio of dansylated nucleoside to the phosphonylation reagent was 1 to 1–10, preferably 1 to 2–8, in particular 1 to 5.

The compounds of the formula (VIIIa) or (VIIIb) obtained in this way can subsequently be employed for the oligonucleotide synthesis. For this, the sugar residues of the nucleotides are deoxyribose for the DNA synthesis and ribose for RNA synthesis, but mixtures of deoxyribose and ribose can also be used for synthesizing an oligonucleotide composed of regularly or irregularly arranged deoxyribose and ribose sugar residues. Furthermore, the oligonucleotide can have a regular or irregular structure composed of mononucleotides of the formula (VIIIa) and (VIIIb).

The oligonucleotide synthesis can be carried out by the H-phosphonate method as described, for example, by B. C. Froehler et al. (Froehler, B. C. (1986) Nucleic Acids Res. 14, 5399–5407, No. 13), in which case the acid elimination of the 5'-hydroxyl protective group is replaced by the basic elimination of the dansylethoxycarbonyl group.

The synthesis can in principle be carried out either in solution, for example in analogy to the method of C. B. Reese (1989), or on the solid phase, for example in analogy to the method of B. C. Froehler (1986). The solid-phase synthesis is generally preferred.

The following reaction sequence was preferably chosen for this:

1. Reaction of a compound of the formula (VIIIa) or (VIIIb) with the nucleoside-bonded polymeric support of the formula (VIIa) or (VIIb) in the presence of an acid chloride, for example pivaloyl chloride or adamantoyl chloride
2. Elimination of the dansylethoxycarbonyl group, for example with DBU
3. Reaction of the resulting compound with a compound of the formula (VIIIa) or (VIIIb)
4. Repetition of step 2 and 3 up to the required chain length of the oligonucleotide
5. Oxidation, to the phosphate, phosphoramidate or to the thiophosphate, for example with iodine or sulfur or amine/$CCl_4$/triphenylphosphine (Jäger et al. see above).

The compounds of the formula (VIIIa) or (VIIIb) and (VIIa) and (VIIb) were preferably reacted at a temperature of $-20°$ C. to $+100°$ C., in particular at room temperature in the presence of, for example, pivaloyl chloride as acid. The oxidation was carried out, for example, with iodine in a solvent mixture composed in general of pyridine, N-methylimidazole, water, THF at room temperature.

The oligonucleotides synthesized by the H-phosphonate method described were generally composed of 2 to about 200, preferably 2 to 110, in particular 2 to 40 mononucleotides.

The advantages of oligonucleotide synthesis from dansylated mononucleotides by the phosphoramidite or by the H-phosphonate method are a) the dansyl group is easy to detect because of its strong fluorescence at 550 nm,
b) synthesis of poly- and oligonucleotides down to the picomole range,
c) removal of the 5'-hydroxyl dansyl protective group without elimination of other hydroxyl protective groups on the nucleotide base or on the sugar residue
d) synthesis of oligoribonucleotides and oligodeoxyribonucleotides, especially of oligoribonucleotides,
e) solid-phase synthesis of oligonucleotides in high yields and in large chain lengths.

Another advantage of the use of the 5'-hydroxyl dansyl protective group in RNA synthesis is that the 2'-hydroxyl groups of the ribose residue can remain protected at the end of the synthesis. The oligoribonucleotides modified in this way are thereby generally protected from hydrolysis by RNases but also from possible isomerization reactions and can therefore be stored stable over long periods. The 2'-hydroxyl protective group is generally then only eliminated shortly before use of the RNA.

The elimination from the support, and the cleavage of the amino and hydroxyl protective groups on the synthesized oligonucleotides were carried out by generally known methods, for example as described by M. Gait (ed.):

Oligonucleotide Synthesis, a practical approach; IRL Press; Oxford 1984.

The examples which follow are intended to explain the invention further. The following abbreviations have been used:

Bz for benzoyl
Mthp for methoxytetrahydropyranyl
DansEOC for dansylethoxycarbonyl and
EA for ethyl acetate

EXAMPLE 1

Reaction of 2-dansylethanol with Trichloromethyl Chloroformate 0.8 ml (1.32 g=6.64 mmol) of trichloromethyl chloroformate is pipetted into 10 ml of absolute $CH_3CN$ while cooling in ice and stirring. Then, while cooling in ice and stirring, 1 g (3.58 mmol) of 2-dansylethanol dissolved in 5 ml of absolute $CH_3CN$ is added dropwise with a syringe through a septum. The mixture is stirred in an ice bath for a further 5 h. The precipitated colorless solid is filtered off with suction, washed with absolute tetrahydrofuran and dried under high vacuum. 1.135 g (3.00 mmol=84%) of a colorless solid of melting point 154–55° are obtained.

Elemental analysis shows:

|  | Found | Calculated |
|---|---|---|
| Carbon | 47.90% | 47.63% |
| Hydrogen | 4.64% | 4.53% |
| Nitrogen | 3.96% | 3.70% |

EXAMPLE 2

Reaction of 2'-O-(4-methoxytetrahydropyranyl)-$N^6$-benzoyl-adenosine with 2-dansylethyl Chloroformate Hydrochloride 2.43 g (5 mmol) of 2'-O-Mthp-$N^6$-Bz-adenosine are coevaporated 2× with 30 ml of absolute pyridine each time and then dissolved in 40 ml of absolute pyridine. Then, while cooling in ice and stirring, 2.46 g (6.5 mmol=1.3 eq) 2-dansylethyl chloroformate hydrochloride are added in solid form. The mixture is stirred in an ice bath for 1 h, the hydrochloride dissolving after about 0.5 h. The reaction is then stopped with 0.5 ml (8.8 mmol) of glycol, the mixture is concentrated in a rotary evaporator, diluted with 200 ml of $CH_2Cl_2$ and washed with 200 ml of saturated $NaHCO_3$ solution, the aqueous phase is extracted 2× with 100 ml of $CH_2Cl_2$ each time, and the combined organic phases are dried with $Na_2SO_4$, filtered and concentrated in a rotary evaporator. They are coevaporated 2× with 100 ml of toluene each time and 2× with 100 ml $CH_2Cl_2$ each time. Purification is carried out on an $SiO_2$ column (100 g, 23×3.5 cm). Flash chromatography elution is carried out with 0.5 l of $CH_2Cl_2$, 1 l of $CH_2Cl_2$/MeOH 100:1 and 1.5 l of $CH_2Cl_2$/MeOH 100:2. The individual product fractions are concentrated in a rotary evaporator and dried under high vacuum. 2.86 g (3.62 mmol=72%) of 5'-substituted and 0.47 g (0.43 mmol=9%) of 3',5'-disubstituted product are obtained, in each case as yellow, highly fluorescent foams.

For the elemental analysis 100 mg of the disubstituted product is purified again on 1 $SiO_2$ plate (40×20 cm) with $CH_2Cl_2$/MeOH 100:2.
Analysis data for 2'-O-(4-methoxytetrahydropyranyl)-5'-O-dansylethoxycarbonyl-$N^6$-benzoyladenosine a) Thin-layer chromatography The thin-layer chromatography was carried out on Schleicher und Schüll silica gel F1500/LS 254 in $CH_2Cl_2$/MeOH (95:5), and an $R_f$ of 0.48 was calculated.

b) UV spectroscopy in methanol:

| +λmax | 257 | 272 | 339 |
|---|---|---|---|
| log$\epsilon_{max}$ | 4.42 | 4.38 | 3.65 | c) Elemental analysis

|  | Found | Calculated with 1 mole of $H_2O$ |
|---|---|---|
| Carbon | 56.58% | 56.43% |
| Hydrogen | 5.46% | 5.48% |
| Nitrogen | 10.28% | 10.39% | d) NMR spectroscopy
in $CDCl_3$ at 250 MHz 9.03 s broad (1) NH, 8.81 s (1) H-8, 8.61 d (2) dansyl H-2, 8.35–8.30 m (2) dansyl H-4, dansyl H-8, 8.23 s (1) H-2, 8.03 d (2) 2H of o-Bz, 7.65–7.50 mm (5) 3H of Bz, dansyl H-3, dansyl H-7, 7.20 d (1) dansyl B-6, 6.20 d (1) H-1', 5.13 t (1) B-2', 4.52–4.32 m (6) $CH_2OCO$, B-3', H-4', H-5', H-5", 3.72 t (2) $SO_2CH_2$, 3.77–3.43 m (4) $CH_2OCH_2$ (Mthp), about 2.90 s broad (1) 3'-OH, 2.89 s (6) $NMe_2$, 2.87 s (3) $OCH_3$, 1.95–1.55 m (4) $CH_2CCH_2$ (Mthp)

Analysis data for 2'-O-(4-methoxytetrahydropyranyl)-3',5'-bis-O-dansylethoxycarbonyl-$N^6$-benzoyladenosine a) Thin-layer chromatography The thin-layer chromatography was carried out on silica gel F1500/LS 254 (Schleicher & Schüll) in $CH_2Cl_2$/MeOH (100:1), and an $R_f$ of 0.35 was calculated.

b) UV spectroscopy in methanol:

| λmax | 254 | 278 | 343 |
|---|---|---|---|
| log$\epsilon_{max}$ | 4.58 | 4.37 | 3.91 | c) Elemental analysis

|  | Found | Calculated |
|---|---|---|
| Carbon | 57.87% | 58.07% |
| Hydrogen | 5.46% | 5.24% |
| Nitrogen | 8.67% | 8.94% | d) NMR spectroscopy
in $CDCl_3$ at 250 MHz 9.05 s broad (1) NH, 8.83 s (1) H-8, 8.69–8.60 2d (2) 2×dansyl H-2, 8.35–8.29 m (4) 2×dansyl H-4, 2×dansyl H-8, 8.22 s (1) H-2, 8.03 d (2) 2H of o-Bz, 7.68–7.50 m (7) 3H of Bz, 2×dansyl H-3, 2×dansyl H-7, 7.24–7.18 2 d superimposed to give t (2) 2×dansyl H-6, 6.13 d (1) H-1', 5.32 t (1) H-2', 5.13–5.11 m (1) H-3', 4.60–4.22 m (7) 2×$CH_2OCO$, H-4', H-5', H-5", 3.77–3.26 m (8) 2×$SO_2CH_2$, $CH_2OCH_2$ (Mthp), 2.89 is (6) $NMe_2$, 2.88 s (6) $NMe_2$, 2.63 s (3) $OCH_3$, 1.78–1.20 m (4) $CH_2CCH_2$ (Mthp)

EXAMPLE 3

Reaction of 2'-O-(4-methoxytetrahydropyranyl)-5'-O-dansylethoxycarbonyl-$N^6$-benzoyladenosine with 2-(4-nitrophenyl)ethyl diisopropylphosphoramidochloridite 1 g (1.264 mmol) of 2'-O-Mthp-5'-O-dansEOC-$N^6$-Bz-adenosine is dissolved in 6 ml of absolute $CH_2Cl_2$, and then 0.86 ml (0.65 g=5.03 mmol=4 eq) of Hünig's base and 0.84 g (2.528 mmol=2 eq) of 2-(4-nitrophenyl)ethyl diisopropylphosphoramidochloridite are added. The mixture is stirred at room temperature under a nitrogen atmosphere and wrapped in aluminum foil to exclude light. After 1¼ h, another 0.42 g (1.264 mmol=1 eq) of phosphitylation reagent is added. After stirring at room temperature for a total of 2.5 h, the mixture is diluted with 75 ml of $CH_2Cl_2$ and washed with 75 ml of saturated $NaHCO_3$ solution, the aqueous phase is back-extracted 4× with 50 ml of $CH_2Cl_2$ each time, and the combined organic phases are dried over $Na_2SO_4$, filtered and concentrated in a rotary evaporator. Purification is by flash chromatography on an $SiO_2$ column (30 g, 12×3 cm), elution with 250 ml of $CH_2Cl_2$, 100 ml of $CH_2Cl_2$/EA 100:1, 100 ml of $CH_2Cl_2$/EA 100:2, 100 ml of $CH_2Cl_2$/EA 100:3, 100 ml of $CH_2Cl_2$/EA 100:5, 100 ml of $CH_2Cl_2$/EA 100:7, 100 ml of $CH_2Cl_2$/EA 9:1, 350 ml of $CH_2Cl_2$/EA 4:1 (reagent), 100 ml of $CH_2Cl_2$/EA 2:1 (product), 100 ml of $CH_2Cl_2$/EA 1:1 (product), 100 ml of $CH_2Cl_2$/EA 1:2 (product) and 100 ml EA (product).

The product fractions are concentrated in a rotary evaporator and dried under high vacuum. 0.955 g (0.878 mmol=70%) of a yellow fluorescent foam is obtained.
Analytical data a) Thin-layer chromatography The thin-layer chromatography was carried out on Schleicher und Schüll silica gel F1500/LS 254 in toluene/EA (1:6), and an $R_f$ of 0.50 was calculated.

b) UV spectroscopy in methanol

| λmax | 261 | 330 | 339 |
|---|---|---|---|
| log$\epsilon_{max}$ | 4.54 | 3.55 | 3.51 | c) Elemental analysis

|  | Found | Calculated |
|---|---|---|
| Carbon | 57.08% | 57.45% |
| Hydrogen | 5.87% | 5.84% |
| Nitrogen | 10.29% | 10.31% | d) NMR spectroscopy

1. $^{31}$P-NMR in $CDCl_3$ at 161.70 MHz
   151.34 ppm s (31%)
   149.47 ppm s (69%)

2. $^1$H-NMR in $CDCl_3$ at 250 MHz 9.07 s broad (1) NH, 8.83 and 8.82 2s (1) H-8, 8.61 d (1) dansyl H-2, 8.35–8.29 m (2) dansyl H-4, dansyl H-8, 8.24 and 8.22 2s (1) H-2, 8.18–8.13 2d (2) 2Ho to phenyl-$NO_2$, 8.03 d (2) 2H from o-Bz, 7.64–7.49 m (5) 3H of Bz, dansyl H-3, dansyl H-7, 7.45–7.38 2d (2) 2H m to phenyl-$NO_2$, 7.19 d (1) dansyl H-6, 6.23 and 6.15 2d (1) H-1', 5.20 and 5.11 2t (1) H-2', 4.48 t (2) $CH_2OCO$, 4.44–4.18 m (4) H-3', H-4', H-5', H-5", 4.10–3.88 m (2) $CH_2OP$, 3.84–3.25 m (6) 2×CH (i-Pr). $CH_2OCH_2$ (Mthp), 3.71 t (2) $SO_2CH_2$, 3.06 t (2) $CH_2$-phenyl-$NO_2$, 2.88 s (6) $NMe_2$, 2.66 and 2.61 2s (3) $OCH_3$, 2.00–1.45 m (4) $CH_2CCH_2$ (Mthp, 1.26–1.12 superimposed d (12) 2×$C(CH_3)_2$ (i-Pr)

EXAMPLE 4

Automatic Oligoribonucleotide Synthesis with 2'-O-(4-methoxytetrahydropyranyl)-5'-O-dansylethoxycarbonyl phosphoramidites. Preparation of the decanucleotide (rAp)$_9$T The syntheses were carried out with a 380 B DNA synthesizer (Applied Biosystems)

Column used: ABI standard column

Support material used: LCAMA-CPG support which is linked to the nucleoside via the 3'-hydroxyl group.

(Reference: K. P. Stengele, W. Pfleiderer Nucleic Acids Res. Symp. Ser. 21, 101 (1989); K. P. Stengele, W. Pfleiderer Tetrahedron Lett. 31, 2549 (1990)).

Loading with thymidine which is linked via the 3'-hydroxyl group to the support; 19 µmol/g Batch size: about 0.6 µmol (determination by trityl elimination).

Synthesis cycle:
1. Condensation with 0.5 M tetrazole and 0.1 M 2'-O-(4-methoxytetrahydropyranyl)-5'-O-dansylethoxycarbonyl-N$^6$-benzoyladenosine 3'-O-phosphoramidite in absolute acetonitrile in accordance with the following pulse sequence:

|  |  | tetrazole | 8 sec. |
| --- | --- | --- | --- |
| Phosphoramidite | + | tetrazole | 4 sec. |
|  |  | tetrazole | 3 sec. |
| Phosphoramidite | + | tetrazole | 3 sec. |
|  |  | tetrazole | 3 sec. |
| Waiting step |  |  | 60 sec. |
| Phosphoramidite | + | tetrazole | 3 sec. |
|  |  | tetrazole | 3 sec. |
| Waiting step |  |  | 700 sec. |

2. Capping of unreacted nucleotide with acetic anhydride/lutidine/THF (1:1:3) and 6.5% dimethylaminopyridine (DMAP) in THF

| Flow-through | 20 sec. |
| --- | --- |
| Waiting step | 30 sec. |

3. Oxidation with I$_2$ solution (1.269 g I$_2$/20 ml H$_2$O/10 ml pyridine/100 ml THF)

| Flow-through | 30 sec. |
| --- | --- |
| Waiting step | 30 sec. |

4. Dansylethoxycarbonyl elimination with 0.1 M DBU in acetonitrile in 2×30 sec. and 8×10 sec. pulsed flows with interpolated 1 sec reverse flushes.

The eluates from the 4th step were collected and the condensation yields were determined on the basis of the 5-dimethylamino-1-naphthyl vinyl sulfone which was formed by means of fluorescence spectroscopy (excitation: 368 nm; emission: 526 nm).

The average stepwise yield was about 98%.

Between the individual steps 1–4 the customary washing steps with acetonitrile and the block and reverse flushes were carried out.

EXAMPLE 5

Synthesis of 5'-O-dansylethoxycarbonyl-protected H-phosphonates 10.75 equivalents of imidazole are dissolved in 5 ml of absolute methylene chloride and then cooled with ice/sodium chloride, and subsequently 3.5 equivalents of PCl$_3$ and 11.25 equivalents of triethylamine are added to the cooled solution. The mixture is stirred while cooling for 15 minutes and then 0.25 mmol (1 equivalent) of 2'-O-(4-methoxytetrahydropyranyl)-5'-O-dansylethoxycarbonyl-N$^6$-benzoyladenosine or 0.25 mmol of 2'-O-(4-methoxytetrahydropyranyl)-5'-O-dansylethoxycarbonyl-N$^6$-para-nitrophenylethyloxycarbonyladenosine (coevaporated 1× with acetonitrile) in 5 ml of absolute methylene chloride is added dropwise with stirring over the course of 10 min.

The ice bath is then removed and the mixture is stirred at room temperature for a further 15 minutes. The reaction solution is subsequently extracted by shaking with 10 ml of 1 M triethylammonium bicarbonate. The phases are separated, the aqueous phase is extracted with 10 ml of CH$_2$Cl$_2$, and the combined organic phases are dried over Na$_2$SO$_4$, filtered and concentrated in a rotary evaporator to a yellow fluorescent foam. It is purified on a short silica gel column (flash chromatography) with a CH$_2$Cl$_2$/MeOH gradient.

EXAMPLE 6

Automatic Oligoribonucleotide Synthesis with 2'-O-(4-methoxytetrahydropyranyl)-5'-O-dansylethoxycarbonyl-ribonucleotide 3'-O-H-phosphonates. Preparation of (rAp)$_9$T The syntheses were carried out with a 380 B DNA synthesizer (Applied Biosystems).

Column used: ABI standard column

Support material used: LCAMA-CPG support (reference: K. P. Stengele, W. Pfleiderer Nucleic Acids Res. Symp. Ser. 21, 101 (1989); K. P. Stengele, W. Pfleiderer Tetrahedron Lett. 31, 2549 (1990)).

Loading with thymidine which is linked via the 3'-hydroxyl group to the support, 19 µmol/g Batch size: about 0.6 µmol (determination by trityl elimination).

Synthesis cycle:
1. Washing with absolute pyridine/acetonitrile (1:1)
2. Reaction with 2'-O-(4-methoxytetrahydropyranyl)-51-O-dansylethoxycarbonyl H-phosphonate (10 mM) and pivaloyl chloride (50 mM) in absolute pyridine/acetonitrile (1:1)
3. Washing with absolute acetonitrile (45 seconds)
4. Dansylethoxycarbonyl elimination with 0.1 M DBU in acetonitrile (2 minutes)
5. Repetition of steps 1 to 4 until the required chain length is reached.
6. Dansylethoxycarbonyl elimination with 0.1 M DBU in acetonitrile (2 minutes) and collection of the eluates
7. Oxidation with I$_2$ (0.1 M) in pyridine/N-methylimidazole/water/THF (5/1/5/90) (2.5 minutes) or with I$_2$ (0.1 M) in triethylamine/water/THF (5/5/90) (2.5 minutes)

The oxidation to the thiophosphate or phosphoramidate was also carried out as described in Uhlmann & Peyman (1990).

The eluates from the 6th step are collected and the condensation yields are determined on the basis of the 5-dimethylamino-1-naphthyl vinyl sulfone which is formed by means of fluorescent spectroscopy (excitation: 368 nm; emission: 526 nm).

The average stepwise yield is about 98%.

We claim:

1. A compound of the formula (Va) or (Vb)

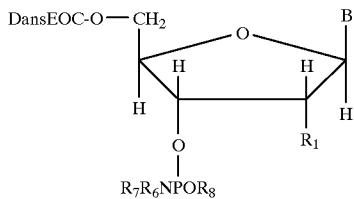

(Va)

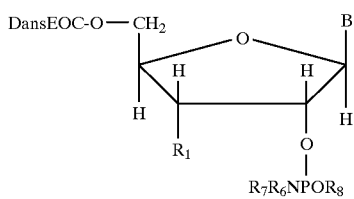

(Vb)

in which:

(i) DansEOC is a group of the formula

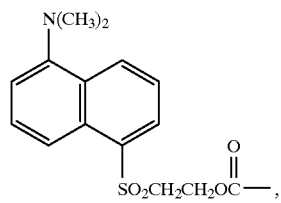

(ii) $R_1$ is selected from the group consisting of

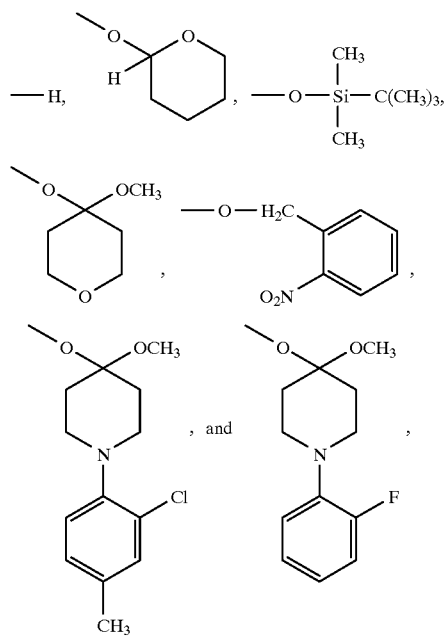

(iii) B is selected from the group consisting of

[structures showing B groups with $NHR_2$, $OR_3$, $R_5$, Y substituents on various purine, pyrimidine, pyrrolopyrimidine, pyrazolopyrimidine, and related heterocyclic bases]

, and

[pyrido-pyrimidinone structure with $R_5$]

;

wherein (A) $R_2$ is selected from the group consisting of

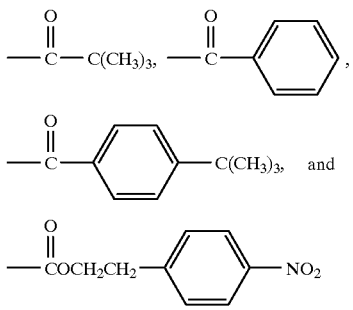

(B) $R_3$ is selected from the group consisting of

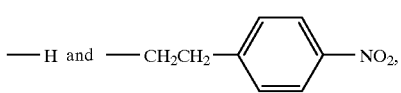

(C) R₄ is selected from the group consisting of

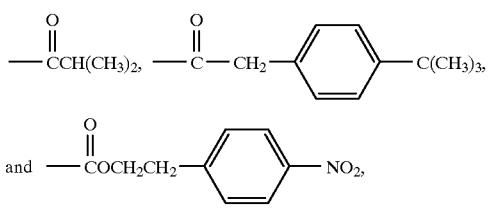

and (D) R₅ is selected from the group consisting of

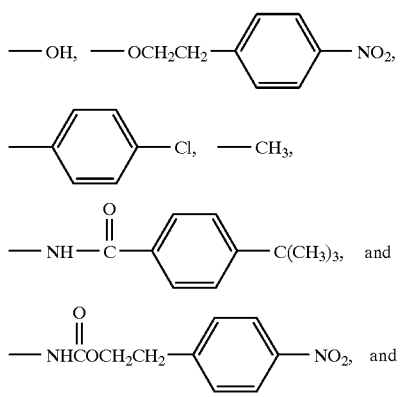

(E) Y is selected from the group consisting of —H, —CH₃, and n-alkyl C₁–C₄;

(iv) R₆ and R₇ are the same or different and are selected from the group consisting of:
a C₁–C₈-alkyl group, a C₅–C₁₂-cycloalkyl group, a benzyl group, and a phenyl group, or, alternatively, R₆ and R₇, together with the nitrogen atom to which they are bonded, form a substituted or unsubstituted, saturated or unsaturated, heterocyclic ring; and (v) R₈ is selected from the group consisting of

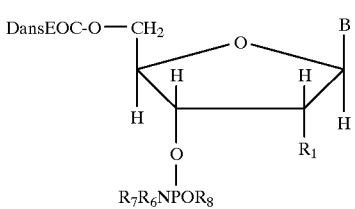

an unsubstituted benzyl group, and a ring-substituted benzyl group, where the substituent(s), independently of one another, are selected from the group consisting of a halogen, a C₁–C₄-alkyl group, nitro, methoxy, and a carboxyl group.

2. A process for the preparation of a compound of the formula (Va) or (Vb)

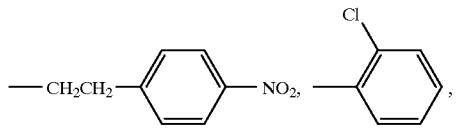 (Va)

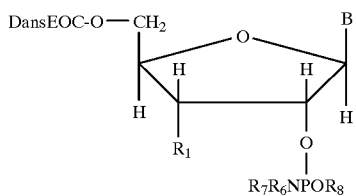 (Vb)

which comprises (a) reacting a compound of the formula (IIIa) or (IIIb)

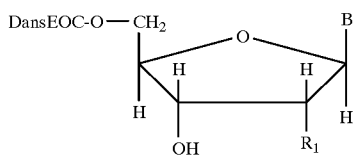 (IIIa)

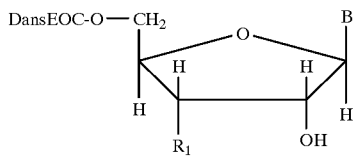 (IIIb)

in which:

(i) DansEOC is a group of the formula

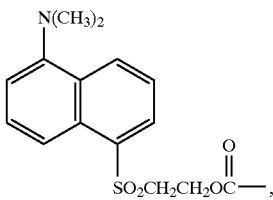

(ii) R₁ is selected from the group consisting of

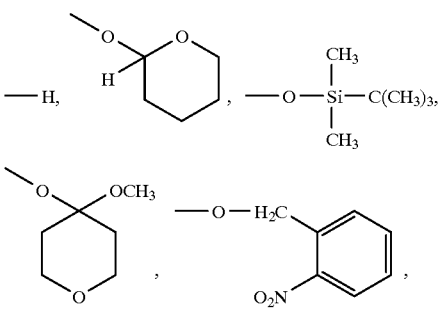

-continued

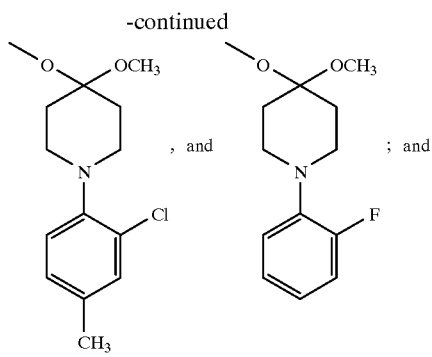
, and ; and (iii) B is selected from the group consisting of

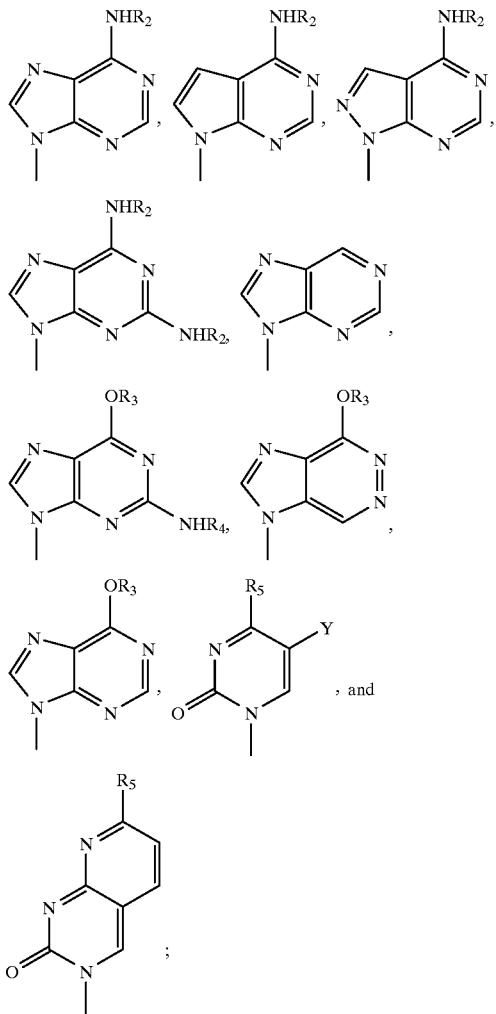

wherein (A) $R_2$ is selected from the group consisting of

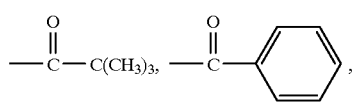

-continued

(B) $R_3$ is selected from the group consisting of

—H and —CH$_2$CH$_2$—⟨phenyl⟩—NO$_2$, (C) $R_4$ is selected from the group consisting of

(D) $R_5$ is selected from the group consisting of

—OH, —OCH$_2$CH$_2$—⟨phenyl⟩—NO$_2$,

—NH—C(=O)—⟨phenyl⟩—C(CH$_3$)$_3$, and

—NHCOCH$_2$CH$_2$—⟨phenyl⟩—NO$_2$, and (E) Y is selected from the group consisting of —H, —CH$_3$, and n-alkyl $C_1$–$C_4$;

(b) in the presence of a base with a compound of the formula (VI)

$$\underset{R_7R_6NPOR_8}{\overset{Z}{|}}$$
(VI)

in which:

(i) $R_6$ and $R_7$ are the same or different and are selected from the group consisting of $C_1$–$C_8$-alkyl, $C_5$–$C_{12}$ cycloalkyl, benzyl, and phenyl, or, alternatively, $R_6$ and $R_7$, together with the nitrogen atom to which they are bonded, form a substituted or unsubstituted, saturated or unsaturated heterocyclic ring, (ii) $R_8$ is selected from the group consisting of

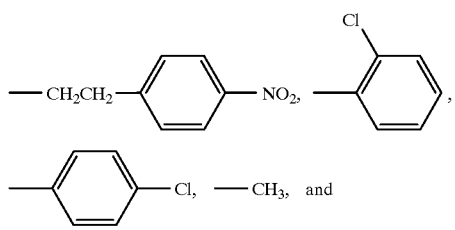

an unsubstituted benzyl group, and a ring-substituted benzyl group, where the substituent(s) are selected from the group consisting of a halogen, a $C_1$–$C_4$-alkyl group, nitro, methoxy, and a carboxyl group, and (iii) Z is selected from the group consisting of chlorine, bromine, and a radical of the formula —$NR_9R_{10}$, where $R_9$ and $R_{10}$ are the same or different and are selected from the group consisting of $C_1$–$C_8$-alkyl, $C_5$–$C_{12}$ cycloalkyl, benzyl group, and phenyl.

3. In a process for the preparation of oligonucleotides, the improvement which comprises:

reacting a compound of the formula (Va) or (Vb)

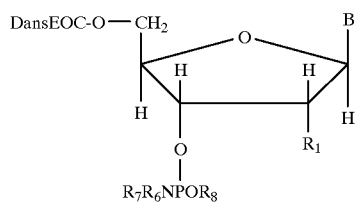

(Va)

(Vb)

in which:

(i) DansEOC is a group of the formula

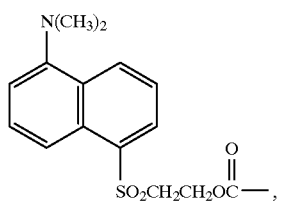

(ii) $R_1$ is selected from the group consisting of

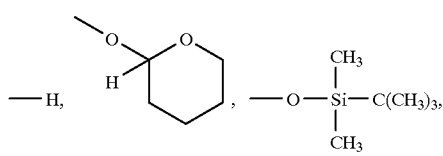

-continued

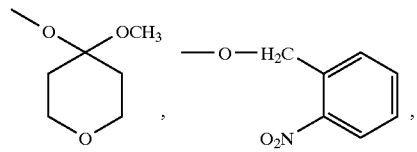

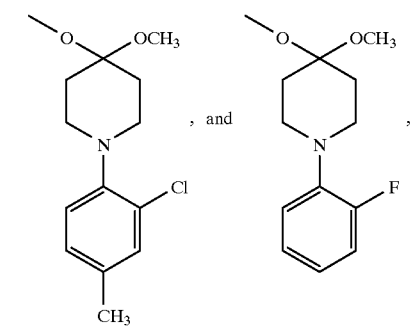

(iii) B is selected from the group consisting of

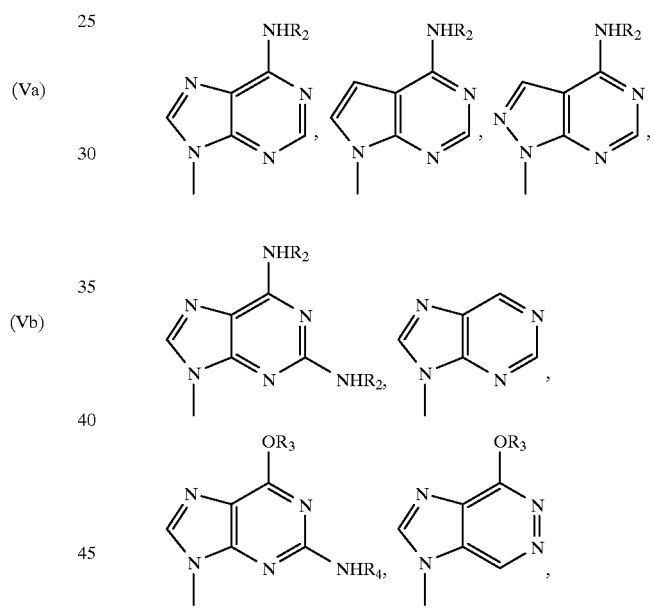

wherein (A) $R_2$ is selected from the group consisting of

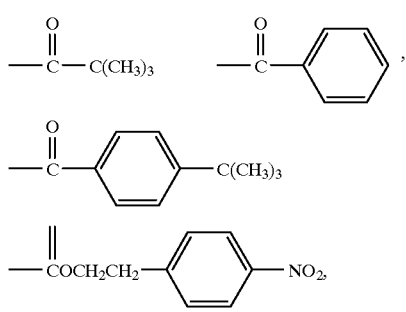

(B) $R_3$ is selected from the group consisting of

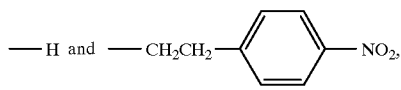

(C) $R_4$ is selected from the group consisting of

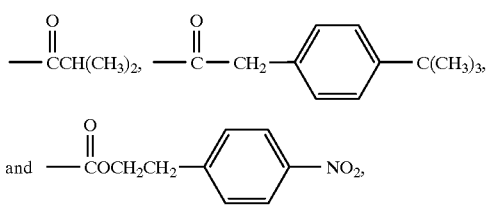

(D) $R_5$ is selected from the group consisting of

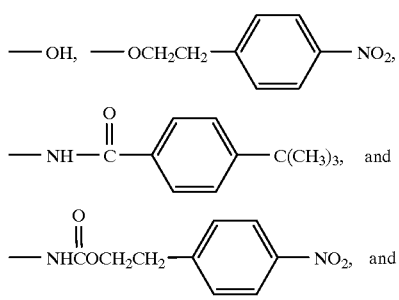

(E) Y is selected from the group consisting of —H, —CH$_3$, and n-alkyl $C_1$–$C_4$;

(iv) $R_6$ and $R_7$ are the same or different and are selected from the group consisting of:
a $C_1$–$C_8$-alkyl group, a $C_5$–$C_{12}$-cycloalkyl group, a benzyl group, and a phenyl group, or, alternatively, $R_6$ and $R_7$, together with the nitrogen atom to which they are bonded, form a substituted or unsubstituted, saturated or unsaturated, heterocyclic ring; and (v) $R_8$ is selected from the group consisting of

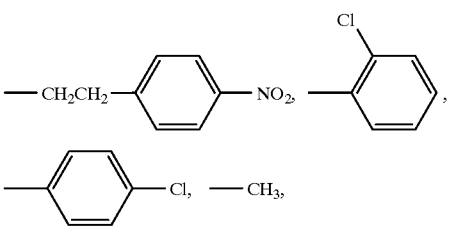

an unsubstituted benzyl group, and a ring-substituted benzyl group, where the substituent(s), independently of one another, are selected from the group consisting of a halogen, a $C_1$–$C_4$-alkyl group, nitro, methoxy, and a carboxyl group;

to form an oligonucleotide comprising said compound of the formula (Va) or (Vb).

4. A compound of the formula (VIIIa) or (VIIIb)

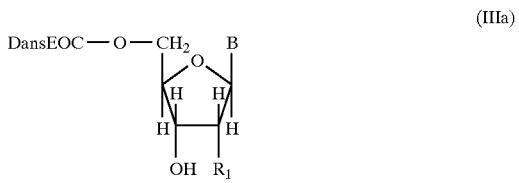

(IIIa)

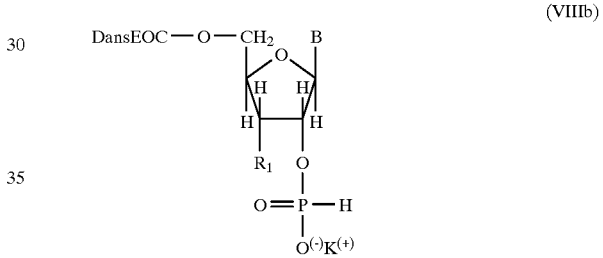

(VIIIb)

in which:

(i) DansEOC is a group of the formula

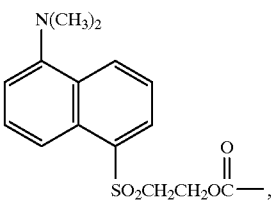

(ii) $R_1$ is selected from the group consisting of

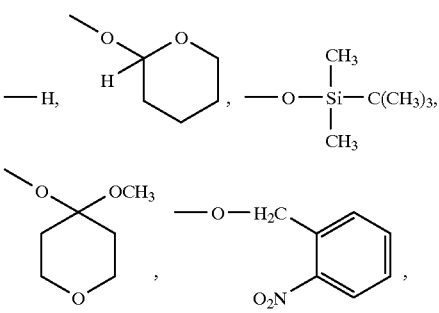

-continued

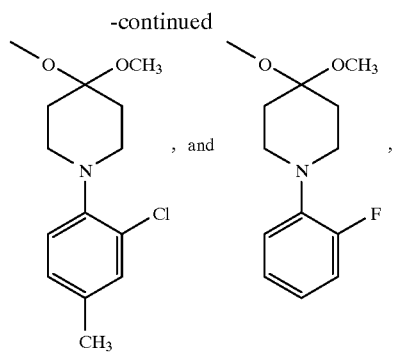, and (iii) B is selected from the group consisting of

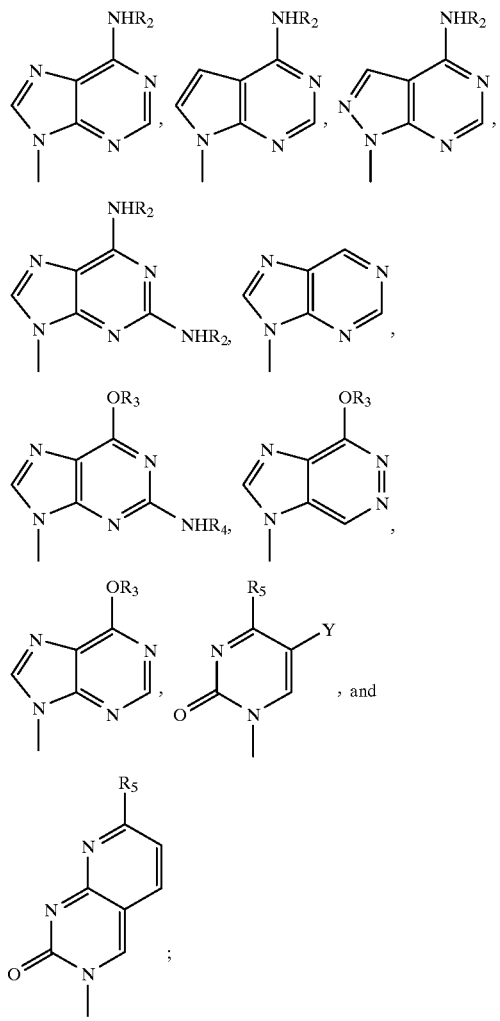

wherein (A) $R_2$ is selected from the group consisting of

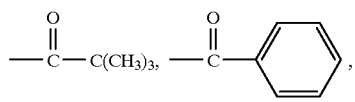

-continued

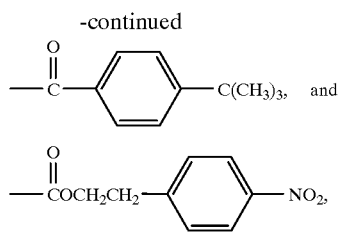

(B) $R_3$ is selected from the group consisting of

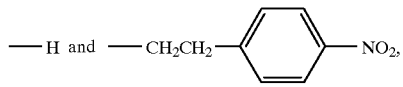

(C) $R_4$ is selected from the group consisting of

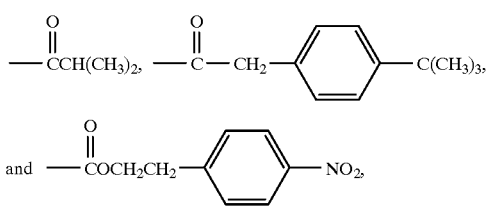

(D) $R_5$ is selected from the group consisting of

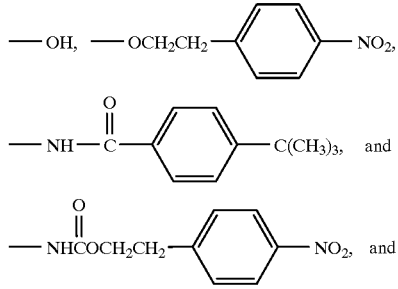

(E) Y is selected from the group consisting of —H, —CH$_3$, and n-alkyl C$_1$–C$_4$; and (iv) $K^{(+)}$ is a cation.

5. A process for the preparation of a compound of the formula (VIIIa) or (VIIIb)

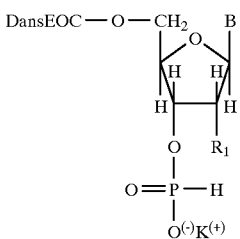

(VIIIa)

(VIIIb)
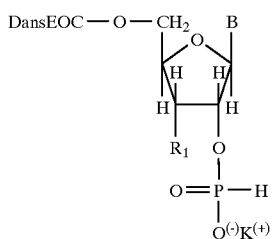
which comprises:
(a) reacting a compound of the formula (IIIa) or (IIIb)
(IIIa)
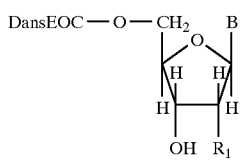
(IIIb)
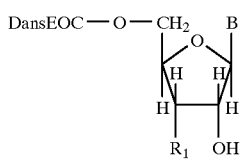
in which:
(i) DansEOC is a group of the formula
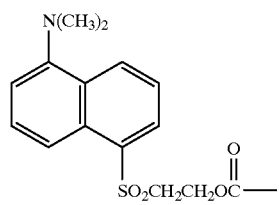
(ii) $R_1$ is selected from the group consisting of
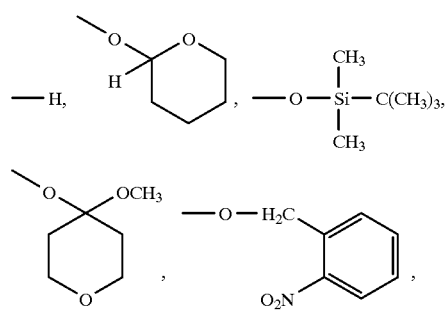
, and                    ; and
(iii) B is selected from the group consisting of
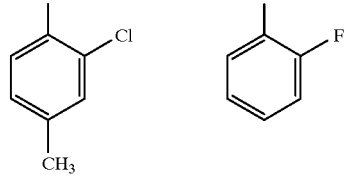
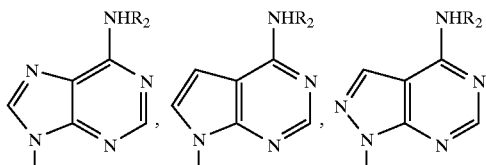
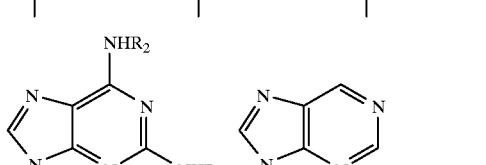
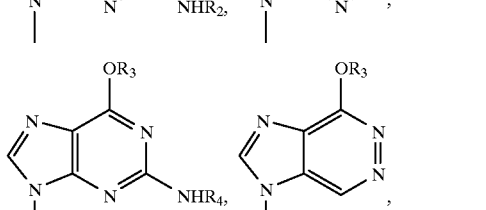
, and
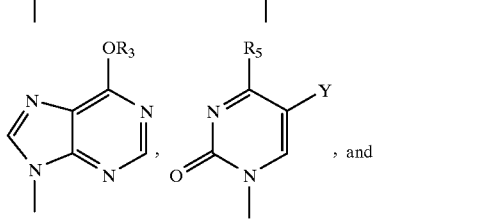
wherein
(A) $R_2$ is selected from the group consisting of
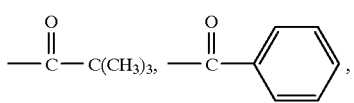

-continued

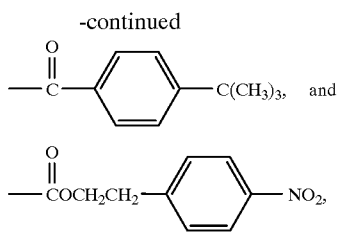

(B) R₃ is selected from the group consisting of

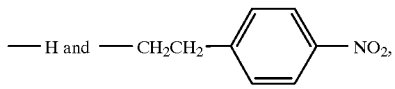

(C) R₄ is selected from the group consisting of

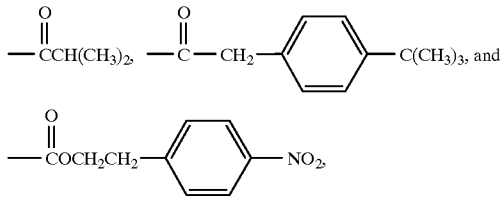

(D) R₅ is selected from the group consisting of

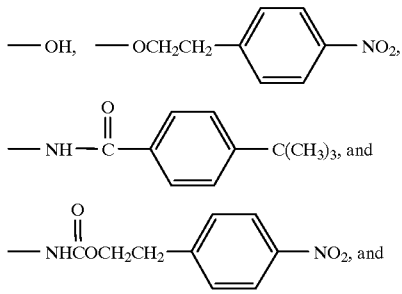

(E) Y is selected from the group consisting of —H, —CH₃, and n-alkyl $C_1$–$C_4$;

(iv) and where K⁺ is a cation;

(b) in the presence of a base, with a compound of the formula (IX)

$$PR_{14}R_{15}R_{16} \qquad (IX)$$

in which $R_1$, $R_{15}$, and $R_{16}$ are the same or different and are selected from the group consisting of hydrogen, a $C_1$–$C_8$-alkyl group, a $C_1$–$C_8$-fluoroalkyl group, and an aryl group.

6. A process for the preparation of a compound of the formula (VIIIa) or (VIIIb)

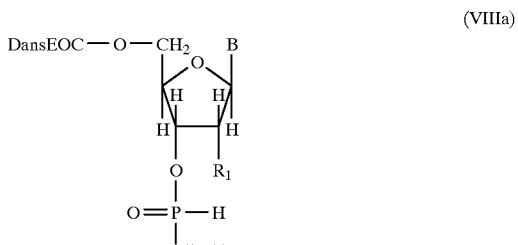

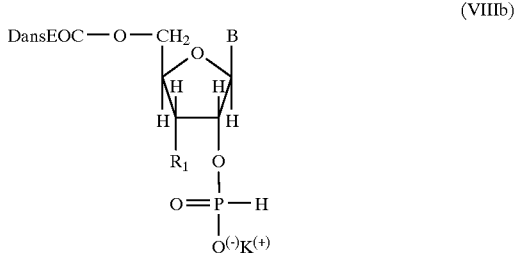

which comprises:

(a) reacting a compound of the formula (IIIa) or (IIIb)

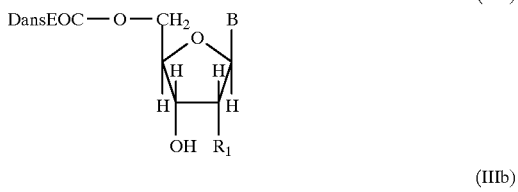

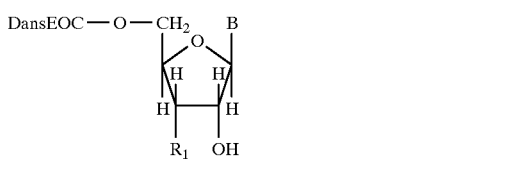

in which:

(i) DansEOC is a group of the formula

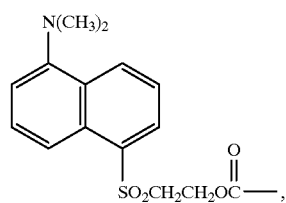

(ii) $R_1$ is selected from the group consisting of

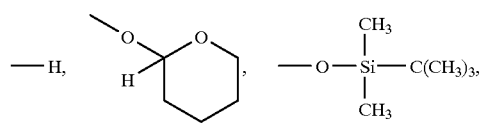

-continued

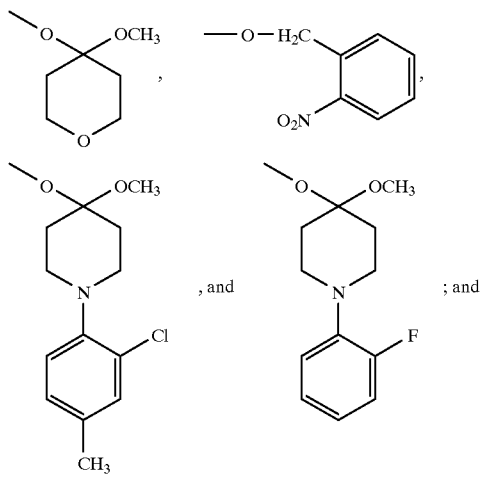

(iii) B is selected from the group consisting of

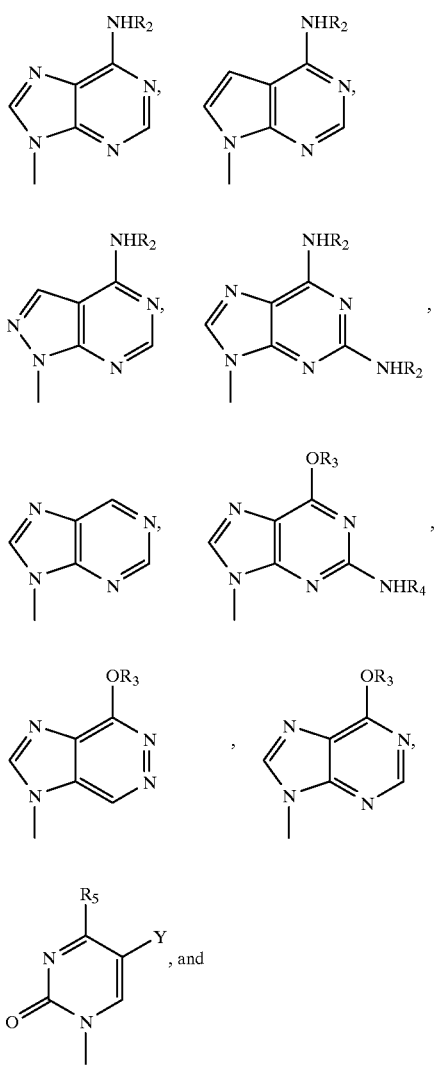

wherein (A) $R_2$ is selected from the group consisting of

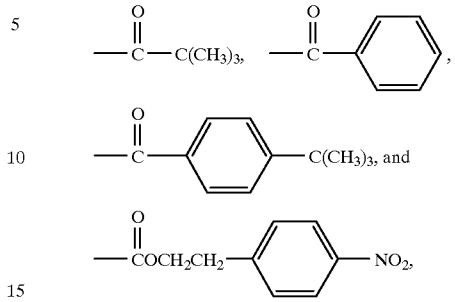

(B) $R_3$ is selected from the group consisting of

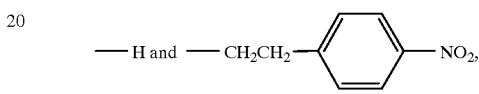

(C) $R_4$ is selected from the group consisting of

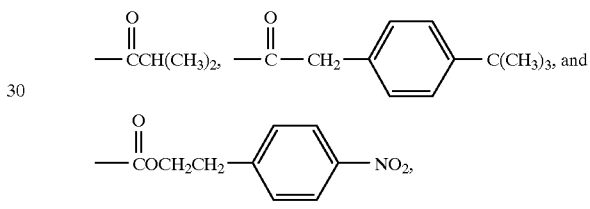

(D) $R_5$ is selected from the group consisting of

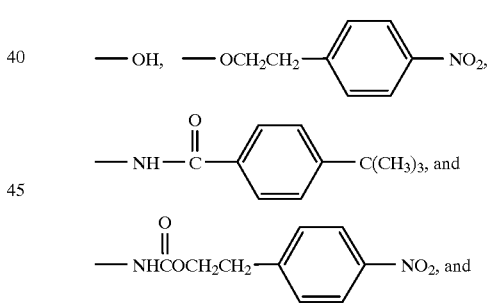

(E) Y is selected from the group consisting of —H, —CH$_3$, and n-alkyl $C_1$–$C_4$;

(iv) and where K$^+$ is a cation;

(b) in the presence of a base, with a compound of the formula (X)

$$PR_{17}R_{18}R_{19} \qquad (X)$$

in which $R_{17}$, $R_{18}$, and $R_{19}$ are the same or different and are selected from the group consisting of chlorine, bromine, a $C_1$–$C_8$-alkylamino group, and a 1,2,4-triazolyl group; and (c) hydrolyzing the resulting product.

7. In a process for protecting a hydroxyl group during oligonucleotide synthesis, the improvement which comprises reacting a compound of the formula (I)

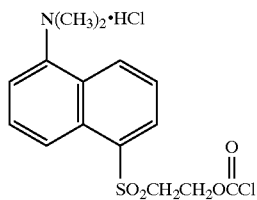 (I)

with said hydroxyl group such that said hydroxyl group is protected during oligonucleotide synthesis.

8. In a process for the synthesis of oligonucleotides, the improvement which comprises reacting a compound of formula (IIIa) or (IIIb)

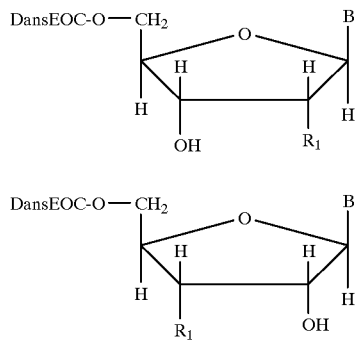

in which:

(i) DansEOC is a group of the formula

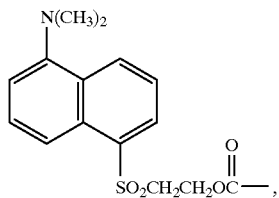

(ii) $R_1$ is selected from the group consisting of:

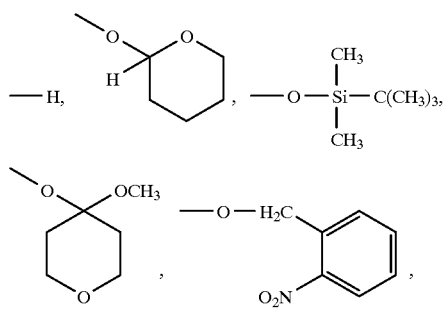

(iii) B is selected from the group consisting of:

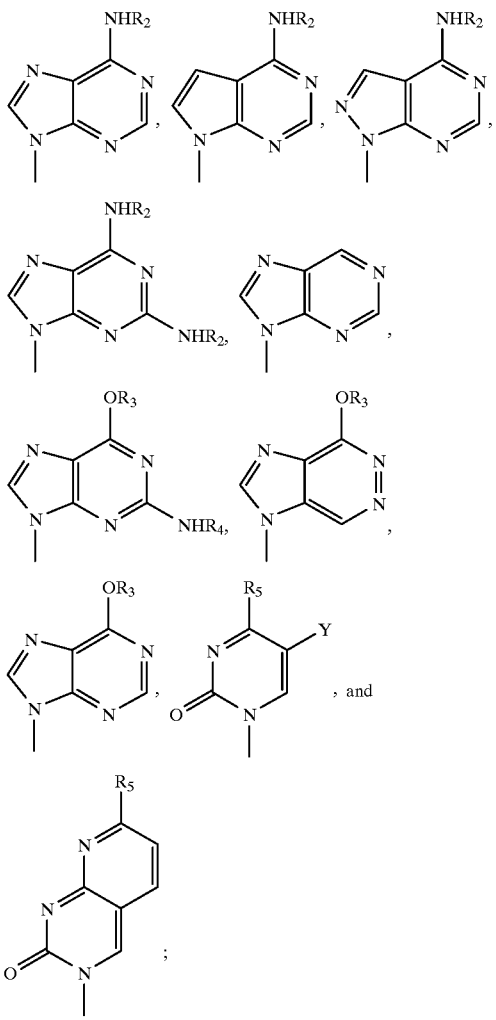

wherein (A) $R_2$ is selected from the group consisting of:

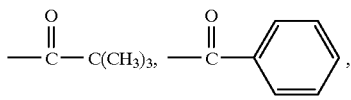

-continued

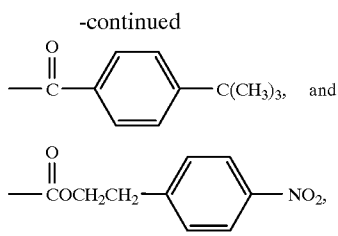

(B) $R_3$ is selected from the group consisting of:

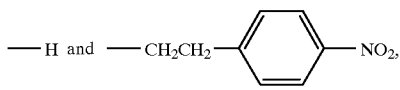

(C) $R_4$ is selected from the group consisting of

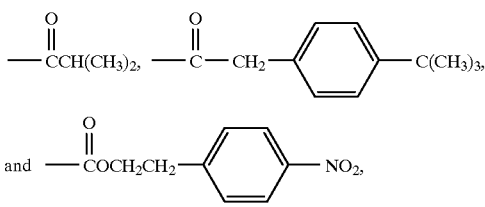

(D) $R_5$ is selected from the group consisting of

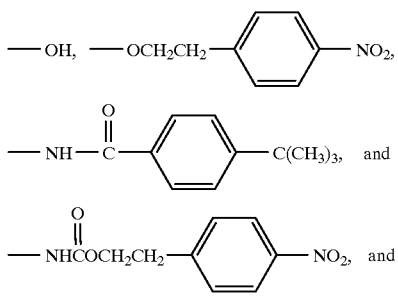

(E) Y is selected from the group consisting of —H, —CH$_3$, and n-alkyl $C_1$–$C_4$, to form an oligonucleotide comprising said compound of the formula (IIIa) or (IIIb).

9. A compound of the formula (Va) or (Vb) as claimed in claim 1, in which $R_6$ and $R_7$ are the same or different and are selected from the group consisting of an isopropyl group and a $C_5$–$C_8$ cycloalkyl group.

10. A process as claimed in claim 2, in which $R_6$ and $R_7$, independently of one another, are selected from the group consisting of an isopropyl group and a $C_5$–$C_8$ cycloalkyl group.

11. A process as claimed in claim 2 in which Z is chlorine.

12. A process as claimed in claim 2, in which said base comprises
  (a) a pyridine, or
  (b) a mixture of tetrahydrofuran, dioxane, methylene chloride, chloroform, and/or acetonitrile with
    (i) a $C_1$–$C_4$-trialkylamine or (ii) tetrazole.

13. A process as claimed in claim 12, in which said $C_1$–$C_4$-trialkylamine is selected from the group consisting of trimethylamine, triethylamine, or diisopropylethylamine.

14. A process as claimed in claim 12, in which Z is a radical of the formula —NR$_9$R$_{10}$ and said $C_1$–$C_4$-trialkylamine has the formula HNR$^{11}$R$^{12}$R$^{13(+)}$X$^{(-)}$, where one or more of R$^{11}$, R$_{12}$ and R$_{13}$ are the same or different and are a $C_1$–$C_4$-alkyl group, and X is a halogen.

15. A process as claimed in claim 14, in which X is chlorine.

16. A process as claimed in claim 12, in which said base comprises a mixture of tetrahydrofuran, dioxane, methylene chloride, chloroform, and/or acetonitrile with tetrazole.

17. A process for the preparation of oligonucleotides, which comprises:
  (a) reacting a compound of the formula (Va) or (Vb) as claimed in claim 1
  (b) with a compound of the formula (VIIa) or (VIIb)

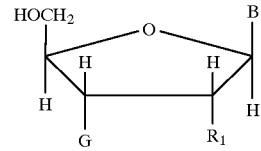

(VIIa)

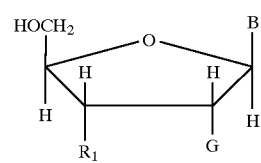

(VIIb)

wherein G has the same meaning as $R_1$ or is a polymeric support which is bonded via the 2'-hydroxyl or 3'-hydroxyl group of said compound of the formula (VIIa) or (VIIb),
  (c) oxidizing the resulting compound,
  (d) eliminating the dansylethoxycarbonyl group,
  (e) reacting the resulting compound with a compound of the formula (Va) or (Vb) as claimed in claim 1, and
  (f) repeating steps (c), (d), and (e) until the desired chain length is obtained.

18. A process as claimed in claim 17, in which said compound of the formula (Va) or (Vb) is reacted with said compound of the formula (VIIa) or (VIIb) at a temperature of –20 to +100° C.

19. A process as claimed in claim 18, in which said temperature is room temperature.

20. A process as claimed in claim 17, wherein the reaction is carried out in the presence of a weak acid.

21. A process as claimed in claim 17, wherein the reaction is carried out in the presence of tetrazole or p-nitrophenyltetrazole.

22. A process as claimed in claim 17, wherein the oxidation is carried out with iodine, sulfur, or iodine in the presence of an amine.

23. A process as claimed in claim 17, wherein the oxidation is carried out at a temperature of –80 to +100° C.

24. A process as claimed in claim 23 wherein said temperature is –20 to +60° C.

25. A process as claimed in claim 23, wherein said temperature is room temperature.

26. A dansylethoxycarbonyl-protected oligonucleotide comprising at least one compound of the formula (Va) or (Vb) as claimed in claim 1.

27. An oligonucleotide prepared from at least one compound of the formula (Va) or (Vb) as claimed in claim 1.

28. A compound as claimed in claim 4, in which K$^{(+)}$ is [HN(C$_2$H$_5$)$_3$]$^{(+)}$.

29. A process as claimed in claim 5, in which $R_{14}$, $R_{15}$, and $R_{16}$ can be the same or different and are selected from the group consisting of a 2,2,2-trifluoroethyl group, a 1,1,1,3,3,3,-hexafluoro-2-propyl group, an ethyl group, and a phenyl group.

30. A process as claimed in claim 6, in which one or more of $R_{17}$, $R_{18}$, and $R_{19}$, is a 1,2,4-triazolyl group.

31. A process as claimed in claim 6, wherein said base is $C_1$–$C_4$-trialkylamine or N-$C_1$–$C_4$-alkylmorpholine.

32. A process as claimed in claim 31, wherein said base is N-methylmorpholine.

33. In a process for the preparation of oligonucleotides, the improvement which comprises reacting a compound of the formula (VIIIa) or (VIIIb) as claimed in claim 6 to form an oligonucleotide comprising said compound of the formula (VIIIa) or (VIIIb).

34. A process for the preparation of oligonucleotides, which comprises:

(a) reacting a compound of the formula (VIIIa) or (VIIIb) as claimed in claim 6, (b) with a compound of the formula (VIIa) or (VIIb),

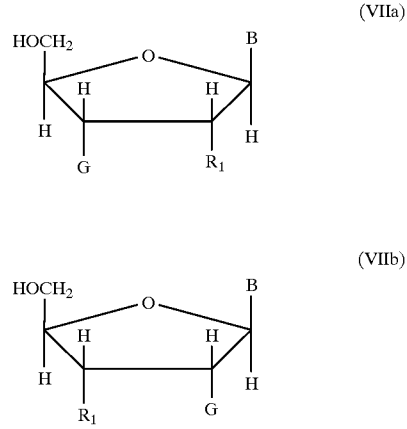

where G has the same meaning as $R_1$ or is a polymeric support which is bonded via the 2'-hydroxyl or 3'-hydroxyl group of said compound of the formula (VIIa) or (VIIb), (c) eliminating the dansylethoxycarbonyl group, (d) reacting the resulting compound with a compound of the formula (VIIIa) or (VIIIb), (e) repeating steps (c) and (d) until the desired chain length is obtained, and (f) oxidizing the resulting oligonucleotide.

35. A process as claimed in claim 34, wherein the compound of the formula (VIIIa) or (VIIIb) is reacted with the compound of the formula (VIIa) or (VIIb) at a temperature of −20 to +100° C.

36. A process as claimed in claim 35, wherein said temperature is room temperature.

37. A process as claimed in claim 34, wherein the reaction is carried out in the presence of an acid halide.

38. A process as claimed in claim 37, wherein said acid halide is an acid chloride.

39. A process as claimed in claim 34, wherein the reaction is carried out in the presence of pivaloyl chloride or adamantanecarbonyl chloride.

40. A process as claimed in claims 34, wherein the oxidation is carried out with iodine, sulfur, or an amine in the presence of triphenylphosphine/$CCl_4$.

41. A dansylethoxycarbonyl-protected oligonucleotide prepared from at least one compound of the formula (VIIIa) or (VIIIb) as claimed in claim 6.

42. An oligonucleotide prepared from at least one compound of the formula (VIIIa) or (VIIIb) as claimed in claim 6.

* * * * *

UNITED STATES PATENT AND TRADEMARK OFFICE
CERTIFICATE OF CORRECTION

PATENT NO.   : 5,945,524
DATED        : August 31, 1999
INVENTOR(S)  : Pfleiderer et al.

It is certified that error appears in the above-identified patent and that said Letters Patent is hereby corrected as shown below:

Column 33,
Line 61, "$R_1$," should read -- $R_{14}$, --.

Column 35,
Line 65, after " 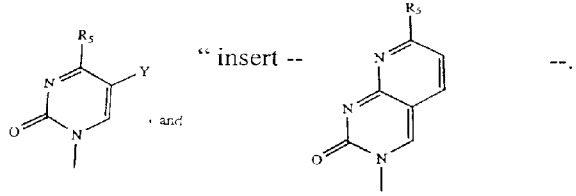 " insert -- -- .

Column 36,
Line 65, "protecting a hydroxyl group" should read -- protecting a 5' hydroxyl group of an oligonucleotide --.

Column 40,
Line 2, "$R^{11}$, $R_{12}$ and $R_{13}$" should read -- $R^{11}$, $R^{12}$ and $R^{13}$ --.
Line 65, "$HN(C_2H_5)_3]$" should read -- $[HN(C_2H_5)_3]$ --.

Signed and Sealed this

Eighth Day of October, 2002

*Attest:*

*Attesting Officer*

JAMES E. ROGAN
*Director of the United States Patent and Trademark Office*